United States Patent [19]

Goemans

[11] Patent Number: Plant 7,077

[45] Date of Patent: Dec. 19, 1989

[54] ALSTROEMERIA PLANT NAMED GOLDEN DELIGHT

[75] Inventor: Frank Goemans, Chichester, England

[73] Assignee: Wuelfinghoff Freesia B.V., Netherlands

[21] Appl. No.: 294,254

[22] Filed: Jan. 6, 1989

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An Alstroemeria plant named Golden Delight having yellow to dark yellow flowers. There is no streaking on the outer surfaces of the petals, but there are medium to heavy red-purple streaks on the inner and upper surfaces of the inner flower petals.

1 Drawing Sheet

1

The present invention comprises a new and distinct cultivar of Alstroemeria plant known by the cultivar name Golden Delight.

Golden Delight was originated by the inventor Frank Goemans from a hybridization made in a controlled breeding program in Chichester, Sussex, United Kingdom in 1984. The female parent was a cultivar identified as 416, a cultivar of unknown origin. The male parent of Golden Delight was a cultivar identified as 813, a selection from the Alstroemeria species *A. aurantiaca.*

Golden Delight was discovered and selected as one flowering plant within the progeny of the stated parentage by Frank Goemans on June 23, 1984 in a controlled environment in Chichester, Sussex, United Kingdom.

The first act of asexual reproduction of Golden Delight was accomplished when vegetative cuttings were taken from the initial selection on July 7, 1984 in a controlled environment in Chichester, United Kingdom by Frank Goemans. Horticultural examination of selected units initiated June 27, 1986 has demonstrated that the combination of characteristics as herein disclosed for Golden Delight are firmly fixed and retained through generations of asexual reproduction.

Golden Delight has not been observed under all possible environmental conditions. The phenotype may vary significantly with variations in environment such as temperature, light intensity and day length. The following observations, measurements and comparisons describe plants grown in Spalding Lincs, United Kingdom under greenhouse conditions which approximate those generally used in commercial practice.

The following traits have been repeatedly observed and are determined to be basic characteristics of Golden Delight which in combination distinguish this Alstroemeria as a new and distinct cultivar:

1. Yellow to dark yellow flowers.
2. No streaking on the outer surface of the flowers, with the term outer surface being synonymous with the term under surface in these generally lily shaped flowers.
3. Medium to heavy streaking occurs on the inner and upper surfaces of the inner flower petals, with the streaking being red-purple in color.

Of the many commercial cultivars known to the present inventor, the most similar in comparison to Golden Delight is Lima. In comparison to Lima, Golden Delight has heavier stripes on the inner flower petals, with the stripes being a somewhat lighter red-purple in color.

2

The accompanying photographic drawing shows typical inflorescence and foilage characteristics of Golden Delight, with colors being as nearly true as possible with illustrations of this type. The photograph comprises a closeup showing an open flower, an unopened bud, and foilage.

In the following description, color references are made to The Royal Horticultural Society Color Chart. The color values were determined in the afternoon of May 21, 1986 under natural light conditions at Spalding, United Kingdom.

Classification:
- *Botanical.*—Alstroemeria cv Golden Delight.
- *Commercial.*—Alstroemeria.

PLANT

Form: Normal.
Height: Typically reaches 65 inches.
Growth: Vigorous.
Foliage:
- *Quantity.*—Medium.
- *Size of leaf.*—7×1.5 inches.
- *Shape of leaf.*—Elliptic.
- *Color.*—Upperside, medium green; underside, medium green.

Rhizomes:
- *Color.*—White.
- *Size.*—Normal.

INFLORESCENCE

A. Bud:
- *Form.*—Normal.
- *Diameter.*—One-half inch.
- *Length.*—One and one-half inch.
- *Calyx.*—Elliptic.

B. Flower:
- *Size.*—Approximately 3 inches in diameter.
- *Borne.*—Medium number of branches in umbel.
- *Blooming habit.*—Medium to heavy.
- *Shape.*—Normal.
- *Color.*—Upper surface: Approximately 14AB. Under Surface: Between 17A and 21A.
- *Streaking.*—On inside petals only, red-purple in color to provide an attractive contrast with the bright yellow flowers.
- *Peduncle.*—Length, 65 inches; color, medium green.

*Lasting Quality.*—Approximately 10 days.

REPRODUCTIVE ORGANS

Stamens: Number, 6.
Anthers: Color, yellow-green.
Filaments: Color, pink-pale.

Pistils: Number, 1; Color, light green.
Stigma: Color, yellow.

I claim:

1. A new and distinct cultivar of Alstroemeria plant named Golden Delight, as illustrated and described.

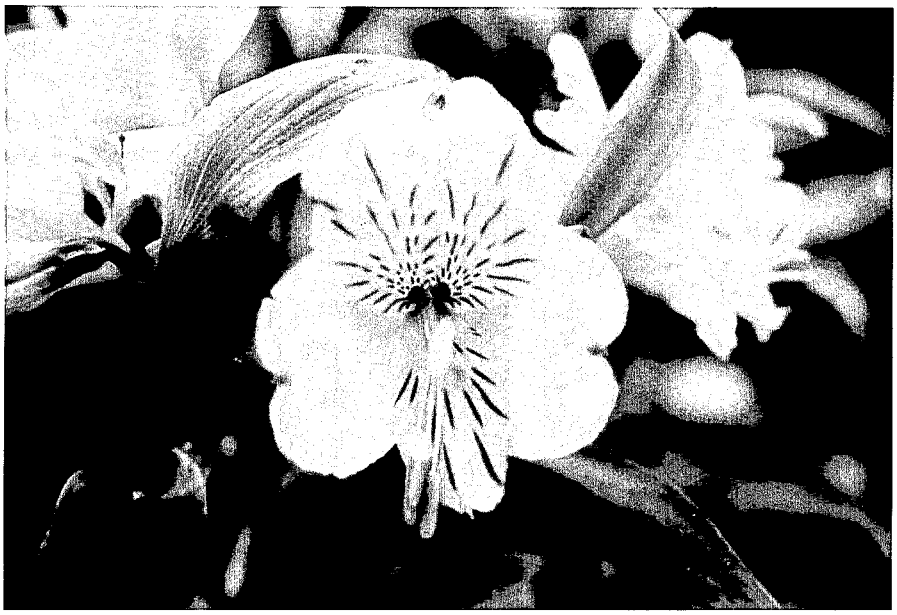

* * * * *